(12) United States Patent
Rubinson

(10) Patent No.: US 9,364,422 B2
(45) Date of Patent: Jun. 14, 2016

(54) STYRENE MALEIC ANHYDRIDE POLYMERS IN COSMETICS AND PERSONAL CARE PRODUCTS

(71) Applicant: Avon Products, Inc., Suffern, NY (US)

(72) Inventor: Emily H. Rubinson, Suffern, NY (US)

(73) Assignee: Avon Products, Inc, New York, NY (US)

( * ) Notice: Subject to any disclaimer, the term of this patent is extended or adjusted under 35 U.S.C. 154(b) by 225 days.

(21) Appl. No.: 14/133,851

(22) Filed: Dec. 19, 2013

(65) Prior Publication Data

US 2015/0174053 A1 Jun. 25, 2015

(51) Int. Cl.
*A61K 8/81* (2006.01)
*A61Q 1/06* (2006.01)
*A61K 8/19* (2006.01)
*A61K 8/92* (2006.01)
*A61K 8/29* (2006.01)

(52) U.S. Cl.
CPC . *A61K 8/922* (2013.01); *A61K 8/19* (2013.01); *A61K 8/29* (2013.01); *A61K 8/8164* (2013.01); *A61Q 1/06* (2013.01); *A61K 2800/43* (2013.01)

(58) Field of Classification Search
CPC .... C08L 35/06; C09D 17/002; C09D 17/004; A61K 8/8164; A61K 8/922; A61K 8/19; A61K 8/29; A61Q 1/06
See application file for complete search history.

(56) References Cited

U.S. PATENT DOCUMENTS

| | | | | |
|---|---|---|---|---|
| 4,665,107 A * | 5/1987 | Micale | ...... | A61K 8/11 424/401 |
| 5,143,723 A * | 9/1992 | Calvo | ...... | A61K 8/84 106/499 |
| 5,310,721 A | 5/1994 | Lo | | |
| 5,320,835 A | 6/1994 | Pahlck et al. | | |
| 5,324,506 A * | 6/1994 | Calvo | ...... | A61K 8/84 424/401 |
| 5,889,088 A | 3/1999 | Kisuno et al. | | |
| 5,948,843 A * | 9/1999 | Boutier | ...... | C08F 8/14 524/313 |
| 6,232,405 B1 * | 5/2001 | Schmidhauser | ...... | C08F 8/32 523/160 |
| 8,129,476 B2 | 3/2012 | Gobelt et al. | | |
| 8,153,731 B2 | 4/2012 | Gobelt et al. | | |
| 2004/0001792 A1 * | 1/2004 | Biatry | ...... | A61K 8/11 424/62 |
| 2004/0052856 A1 | 3/2004 | Stover et al. | | |
| 2009/0155375 A1 * | 6/2009 | Tonge | ...... | A61K 8/553 514/1.1 |
| 2010/0029834 A1 | 2/2010 | Gobelt et al. | | |
| 2010/0179278 A1 | 7/2010 | Ma et al. | | |
| 2010/0322879 A1 | 12/2010 | Gobelt et al. | | |

FOREIGN PATENT DOCUMENTS

| | | | | |
|---|---|---|---|---|
| EP | 0249685 B1 | 1/1993 | | |
| EP | 0889102 A2 * | 1/1999 | ...... | C09D 17/001 |
| GB | 929227 A | 6/1963 | | |
| GB | 931150 A | 7/1963 | | |
| GB | WO 2011064555 A2 * | 6/2011 | ...... | A61K 8/86 |

OTHER PUBLICATIONS

Hollenberg J. Color Cosmetics. Harry's Cosmeticology. Ed. M.M. Reiger. 8th ed. 2000; ch. 26, pp. 543-558.*
SMA® Multi-Functional Resins: Product Bulletin. Sartomer Company (Sep. 2004).*

* cited by examiner

*Primary Examiner* — Bethany Barham
*Assistant Examiner* — Peter Anthopolos
(74) *Attorney, Agent, or Firm* — David M Joyal

(57) ABSTRACT

The invention relates generally to pigmented compositions that, upon the application of water and pressure, exhibit a visible change in one or more optical attributes such as color.

13 Claims, No Drawings

STYRENE MALEIC ANHYDRIDE POLYMERS IN COSMETICS AND PERSONAL CARE PRODUCTS

FIELD OF INVENTION

The invention relates generally to pigmented compositions that, upon the application of water and pressure, exhibit a visible change in one or more optical attributes such as color.

BACKGROUND

The cosmetic and personal care industries have attempted to provide cosmetics that are capable of changing color or generating renewed color intensity. For example, U.S. Pat. No. 5,320,835 describes cosmetic compositions that employ rupturable microcapsules with pigment-containing cores. Those compositions are said to be activated by the application of shear forces to release the pigment. Despite prior efforts, there is a continuing need for compositions that are capable of exhibiting a color change. It is therefore an object of the present invention to provide compositions useful in cosmetics and personal care products that have the ability to renew color, intensify color, or change color.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, the present invention provides compositions capable of changing optical attributes (e.g., color, etc.) and methods for preparing them. It has surprisingly been found that the addition of styrene maleic anhydride copolymers to a pigmented composition, such as a so-called pigment grind, can impart color changing properties to the composition, as well as to a cosmetic or personal care product to which the pigment grind is added. The pigment grind and the cosmetic or personal care product formulation are preferably anhydrous or substantially anhydrous. Upon the application of water and pressure and/or shear (such as rubbing), the compositions undergo a change in one or more optical attributes, including, without limitation, a change in color or hue, renewed color, and/or a change in color intensity.

In one aspect of the invention methods are provided for preparing a composition capable of exhibiting color change, such as a pigment grind. The method generally comprises dispersing, under shear, pigment particulates in a carrier (typically anhydrous) in the presence of a styrene-maleic anhydride copolymer. The pigment grind may comprise from about 20% to about 80% (e.g., from about 40% to about 60%) by weight carrier, from about 20% to about 80% (e.g., from about 40% to about 60%) by weight pigment, and from about 0.5% to about 20% (e.g., from about 2% to about 15% or from about 5% to about 10%) by weight styrene-maleic anhydride copolymer. In one embodiment, the carrier comprises or consists essentially of or consists of an oil or an oleophilic material, such as castor oil. The pigment is not particularly limited and may comprise, for example, one or more of titanium dioxide, iron oxide, FD & C lakes, D & C lakes, and carbon black to name a few. In one embodiment, the pigment comprises iron oxide.

The styrene maleic anhydride copolymer may comprise from about 20% to about 50% (e.g., about 25% to about 45%) maleic anhydride monomers and from about 50% to about 80% (e.g., about 55% to about 75%) styrene monomers.

In one embodiment, the styrene-maleic anhydride copolymer comprises the following repeat unit:

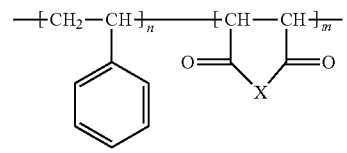

wherein, X comprises a heteroatom such that an anhydride or imide is formed, and in particular X may be selected from —O—, —NH—, or —NR*—, where R* is a $C_{1-12}$ (e.g., $C_{1-6}$) hydrocarbon (e.g., alkyl, alkynyl, aryl, aryl-alkyl, alkyl-aryl, etc.) optionally containing from 1-3 (e.g., one, two, or three) heteroatoms selected from oxygen, sulfur, and nitrogen, and "n" and "m" are each independently integers selected to satisfy the foregoing ratios of maleic anhydride monomer to styrene monomer, and to provide a molecular weight between about 2,500 and about 80,000 (e.g., about 5,000 to about 50,000) Daltons.

In one embodiment, the styrene maleic anhydride copolymer comprises an alternating copolymer. In another embodiment, "n" and "m" are each independently integers selected to provide the foregoing ratios and to provide a molecular weight between about 5,000 and about 10,000 Daltons.

In yet another embodiment, the styrene maleic anhydride copolymer comprises the following repeat unit:

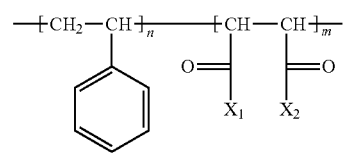

wherein, $X_1$ and $X_2$ are independently selected from —OH, —OZ, —OR—NH$_2$, and —NHR*, wherein R and R* are independently a $C_{1-12}$ hydrocarbon (e.g., $C_1$-$C_8$, $C_2$-$C_6$, etc.) optionally containing from 1-3 heteroatoms (e.g., one two, or three heteroatoms) selected from oxygen, sulfur, and nitrogen, and Z is a cation typically selected from Na$^+$ and NH$_4^+$, where "n" and "m" are each independently integers selected to provide a molecular weight between about 2,500 and about 80,000 Daltons and to provide any of the foregoing monomer ratios. In some embodiments, "n" and "m" are each independently integers selected to provide a molecular weight between about 5,000 and about 10,000 Daltons. In some embodiments, one of $X_1$ or $X_2$ is a group —NH$_2$ and the other of $X_1$ or $X_2$ is —OH. In one embodiment, the styrene-maleic anhydride copolymer comprises an alternating copolymer.

The pressure and/or shear (e.g., rubbing, brushing, combing, etc.) that is applied to the pigment grind may be provided by any suitable means for dispersing the pigment in the carrier, for example, by a three-roll mill.

In another aspect of the invention, a method is provided for achieving a color change in a pigmented composition applied to a human integument (e.g., skin, lips, nails, hair, lashes, etc.). The method comprises applying to the integument a pigmented composition to form a pigmented film on the integument, and then applying water to the film and applying pressure and/or shear (e.g., rubbing) until a change in one or more optical properties (e.g., color, hue, renewed color, etc.) is achieved. The composition that is applied to the integument comprises a pigment composition (e.g., a pigment grind) of the invention that is capable of exhibiting a color change, as described herein and may comprise one or more additional ingredients suitable for the intended product (e.g., waxes, gelling agents, emollients, and film forming polymers, etc.).

These and other aspects of the present invention will become apparent to those skilled in the art after a reading of the following detailed description of the invention, including the appended claims.

DETAILED DESCRIPTION

All terms used herein are intended to have their ordinary meaning unless otherwise provided. All ingredient amounts provided herein are by weight percent of the total composition unless otherwise indicated.

"Substantially anhydrous" as used herein means containing less than 5% water. In other embodiments, the compositions will comprise less than about 2.5% or less than about 1% water. The term anhydrous as used herein means that no water is added to the composition and that only that amount of water absorbed from the atmosphere will be present in the composition.

As used herein, the term "color change" includes any visible change in a color attribute, including without limitation, a change in hue, saturation, and/or brightness, as well as complete, substantial, or partial restoration of an original color. As used herein, the term maleic anhydride monomer is intended to encompass not only maleic anhydrides per se, but also the derivatives thereof identified herein, including without limitation, the maleic anhydride derivatives shown in Formulas (I) and (II). Reference to the percentage of a monomer in the styrene maleic anhydride polymers is given on a molar basis unless otherwise indicated.

By "topically acceptable" is meant that an ingredient is generally regarded as safe and non-toxic for application to a human integument.

It has surprisingly been found that the addition of styrene-maleic anhydride copolymers to a pigmented composition, such as a pigment grind, can impart color changing properties to the composition as well as to a cosmetic or personal care product to which the pigment grind is added. The pigment grind and the cosmetic or personal care product formulation are preferably substantially anhydrous. Upon the application of water and pressure and/or shear (such as rubbing), the cosmetics and personal care products undergo a change in one or more optical attributes, including, without limitation, a change in color or hue, renewed color, and/or a change in color intensity. Suitable cosmetics include, without limitation, color cosmetics (e.g., make-up), such as blush, foundation, lipsticks and lip colors, mascara, eyeliner, eye shadow, nail enamel, and the like.

Without wishing to be bound by any particular theory, it believed that the styrene-maleic anhydride copolymers may, at least partially, encapsulate, agglomerate or encase pigment particles and that when used in a substantially anhydrous cosmetic/personal care product formulation, the addition of water and pressure and/or shear (e.g., rubbing) disrupts the encapsulation or agglomeration and releases or at least partially exposes the pigment particles, providing a renewal or re-emergence of the pigment in the formulation. Particles other than pigments, such as fillers, beads, polymers, SPF-providing particles and the like may also be encapsulated or agglomerated with the styrene-maleic anhydride copolymers of the invention. The particulate materials may be substantially inert in the presence of water or may be reactive with water or in the presence of water.

European Patent No. 0249685 describes colorants and cosmetics that employ polymers, including styrene maleic anhydride polymers, to encapsulate colorants. The contents of that patent are hereby incorporated by reference. The present invention is distinguished from European Patent No. 0249685 at least because the styrene maleic anhydride polymers in that patent are used in aqueous suspensions. That patent also does not disclose any steps in which water and/or pressure are applied to a film formed from the compositions after they are applied to a human integument, to cause a change in any optical property of the compositions.

In one aspect of the invention methods are provided for preparing a pigmented composition, such as a pigment grind, that is capable of exhibiting a color change. The methods comprise dispersing, under shear, pigment particulates in a carrier (typically anhydrous), in the presence of a styrene-maleic anhydride copolymer. Typically, high shear is employed. The dispersing step can be carried out using any suitable mixer, mill, or grinder that provides shear, such as a three-roll mixer, a ball mixer, continuous bead milling, a sand mill, a stone mill, a roller mill, a horizontal mill, and the like. In one embodiment, the pigment grind is prepared in a three-roll mixer. In one embodiment, sufficient grinding of the dispersion will be achieved when a sample measured on a standard Hegeman gauge reads no less than 6.5, indicating a maximum particle size of less than about 30 microns or less than about 20 microns. The Hegeman gauge testing may be carried out according to ASTM D1210-05(2010), which is hereby incorporated by reference. In another embodiment, the viscosity of the resulting dispersion is less than about 4000 cps when measured at about 25° C.

The amount of carrier in a pigment grind is not particularly limited. For example, the pigment grind may comprise from about 20% to about 80% by weight carrier. In other embodiments, the pigment grind comprises from about 25% to about 75% by weight carrier, from about 35% to about 65% by weight carrier, or from about 45% to about 55% by weight carrier. The pigment grind may comprise, for example, from about 20% to about 80% by weight pigment. In other embodiment, the pigment grind comprises from about 25% to about 75% by weight pigment, from about 35% to about 65% by weight pigment, or from about 45% to about 55% by weight pigment. The amount of styrene maleic anhydride copolymer may be any amount sufficient to produce a visible color change on rubbing with water. The pigment grind may comprise, for example, from about 0.5% to about 20% by weight styrene-maleic anhydride copolymer. In other embodiments, the pigment grind comprises from about 1% to about 15% by weight styrene maleic anhydride copolymer, from about 2% to about 10% by weight styrene maleic anhydride copolymer, or from about 5% to about 8% by weight styrene maleic anhydride copolymer.

In one embodiment, the pigment grind comprises, consists essentially of, or consists of from about 20% to about 80% by weight carrier (e.g., castor oil), from about 20% to about 80% by weight pigment (e.g., iron oxide), and from about 0.5% to about 20% by weight styrene-maleic anhydride copolymer. By "consists essentially of" is meant that additional ingredients are excluded in amounts that would affect the basic and novel features of the invention, including, for example, the ability of the compositions to exhibit a visually perceptible color change when a film of the composition is rubbed with water.

The carrier used in the pigment grind is not an aqueous carrier, and is typically anhydrous or substantially anhydrous. In various embodiments, the carrier will comprise less than 5%, less than 4%, less than 3%, less than 2%, less than 1%, or less than 0.5% by weight water. Any suitable oil or oleophilic material may be used alone or in combination as a carrier in the pigment grind, including, without limitation, volatile or non-volatile oils, including without limitation, mineral oil, castor oil, vegetable oil, peanut oil, lanolin oil, squalene, ester oils, such as, without limitation, isopropyl myristate, isopropyl palmitate, lanolin oil, triisocetyl citrate, $C_{10-18}$ triglycerides, caprylic/capric/triglycerides, diisopropyl mimerate, coconut oil, corn oil, cottonseed oil, linseed oil, mink oil, olive oil, palm oil, illipe butter, rapeseed oil, soybean oil, sunflower seed oil, walnut oil, silicone oils such as, for example, linear silicone oil, cyclic silicone oil, and paraffinic hydrocarbons, to name a few. In one embodiment, the carrier used in the pigment grind comprises castor oil.

Any pigment or combination of pigments may be used in the pigment pre-grinds of the invention, so long as the pigments or combination of pigments are capable of exhibiting the requisite color change when present in a grind comprising a substantially anhydrous carrier and a styrene maleic anhydride copolymer. As used herein, the term "pigment" embraces lakes (FD & C and D & C) and fillers such as talc, calcium carbonate, etc. Exemplary inorganic pigments may include, but are not limited to, inorganic oxides (e.g., metal oxides) and hydroxides such as magnesium oxide, magnesium hydroxide, calcium oxide, calcium hydroxides, aluminum oxide, aluminum hydroxide, iron oxides (e.g., $\alpha$-$Fe_2O_3$, $\gamma$-$Fe_2O_3$, $Fe_3O_4$, FeO) and iron hydroxides including red iron oxide, yellow iron oxide and black iron oxide, titanium dioxide, titanium lower oxides, zirconium oxide, chromium oxides, chromium hydroxides, manganese oxides, manganese hydroxides, cobalt oxides, cobalt hydroxides, cerium oxides, cerium hydroxides, nickel oxides, nickel hydroxides, zinc oxides and zinc hydroxides and composite oxides and composite hydroxides such as iron titanate, cobalt titanate and cobalt aluminate and the like. In one embodiment, the inorganic oxide particles may be selected from silica, alumina, zinc oxide, iron oxide, zinc oxide, and titanium dioxide particles, and mixtures thereof. In one embodiment, the pigments have a particle size from 5 nm to 500 microns, or from 10 nm to 100 microns, or from 100 nm to 30 microns or from about 0.75 to 20 microns. In some embodiments, the particle size (median) will be less than about 10 microns, less than about 5 microns or less than 1 micron.

Other suitable colorants contemplated for use in the invention in either the pigment grind or in the final cosmetic or personal care composition, are well known in the art, and are disclosed in the C.T.F.A. Cosmetic Ingredient Handbook, First Edition, 1988, the contents of which are hereby incorporated by reference. Lakes may include, for example, FD&C lakes and D&C lakes. Lakes may include those based on barium, strontium, calcium or aluminum. Additional exemplary color additive lakes include, for example: D&C Red No. 19 (e.g., CI 45170, CI 73360 or CI 45430); D&C Red No. 9 (CI 15585); D&C Red No. 21 (CI 45380); D&C Orange No. 4 (CI 15510); D&C Orange No. 5 (CI 45370); D&C Red No. 27 (CI 45410); D&C Red No. 13 (CI 15630); D&C Red No. 7 (CI 15850:1); D&C Red No. 6 (CI 15850:2); D&C Yellow No. 5 (CI 19140); D&C Red No. 36 (CI 12085); D&C Orange No. 10 (CI 45475); D&C Yellow No. 19 (CI 15985); FD&C Red #40 (CI#16035); FD&C Blue #1 (CI#42090); FD&C Yellow #5 (CI#19140); or any combinations thereof.

Additional suitable particulate colorants may include carbon black, ultramarine blue, ferric blue, Prussian blue, manganese violet, talc, mica, sericite, calcium carbonate, fumed silica, and the like. Suitable pearling pigments include, without limitation, bismuth oxychloride, guanine, and titanated mica.

In one embodiment, the pigment comprises one or more of titanium dioxide, iron oxide, FD & C lakes, D & C lakes, and carbon black. In one embodiment, the pigment comprises iron oxide. The pigments may or may not be encapsulated in silica to impart soft-focus. When used in the pigment pre-grind of the invention, the pigments may or may not be surface modified with hydrophobic and/or hydrophilic moieties, to adjust one or more characteristics of the colorant, such as dispersibility in the vehicle. It is contemplated that superior color change may be achieved by using pigments that are not surface modified, e.g., pigments that are not surface modified with alkyl chains or other hydrophobic treatments. In one embodiment, the pigment grind is free of pigments that are surface modified. In another embodiment, the pigment grind is free of pigments that are hydrophobically modified. In yet another embodiment, the pigment grinds are free of pigments (e.g., iron oxides) that are surface modified with alkylsilanes, including for example with Triethoxy Caprylylsilane or Triethoxy Caprylylsilane, as well as fluoro- and perfluoro-alkyl analogs thereof. In one embodiment, the pigment grind comprises iron oxide particulates that are not surface treated or modified. In another embodiment, at least 50% (or at least 60%, or at least 70%, or at least 80%, or at least 90%) by weight of the particulates in the pigment grind is constituted by iron oxide particulates that have not been surface treated or modified. In another embodiment, all of the particulates in the pigment grind are iron oxide particulates that have not been surface treated or modified.

When additional pigments are added to the cosmetic formulation (as opposed to the pigment grind), it may be desirable to employ surface modified pigments to improve dispersibility, water-resistance, oil-resistance, and the like. In one embodiment, the cosmetic formulations include an additional pigment (other than the pre-grind) which may comprise iron oxide, optionally surface-treated to impart hydrophobicity, with special mention being made of with alkyl silane (e.g., caprylyl silane) coated pigments. In one embodiment, the cosmetic compositions include, in addition to the pigment pre-grind, from about 0.1 to about 10% by weight of additional pigments, lakes, and filler, which optionally may be surface modified, for example by treatment with Triethoxy Caprylylsilane or Triethoxy Caprylylsilane, to adjust one or more characteristics, such as dispersibility in the vehicle.

The styrene-maleic anhydride copolymer used in the methods and compositions of the invention may be composed of different ratios of maleic anhydride monomers to styrene monomers. In one embodiment, the styrene-maleic anhydride copolymer is composed of from about 25% to about 50% maleic anhydride monomers and from about 50% to about 75% styrene monomers. In other embodiments, the styrene-maleic anhydride copolymer is composed of from about 35% to about 45% maleic anhydride monomers and from about 55% to about 65% styrene monomers. In another embodiment, the styrene-maleic anhydride copolymer is composed of about 40% maleic anhydride monomers and about 60% styrene monomers. In one embodiment, the styrene-maleic anhydride copolymer is composed of about 42% maleic anhydride monomers and about 58% styrene monomers. In one embodiment, the styrene maleic anhydride copolymer may comprise up to about 20% of additional monomers (e.g., 0.01 to 10%) provided that the additional monomers do not prevent a visible color change from occurring on rubbing a film in the presence of a sufficient amount of water.

In one embodiment, the styrene-maleic anhydride copolymer used in the methods and compositions of the invention comprises the repeat unit of Formula (I):

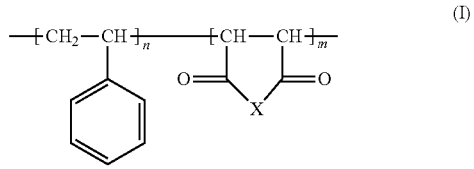

wherein, X is selected from —O—, —NH—, or —NR*—, where R* is a $C_{1-12}$ (e.g., $C_{1-4}$) hydrocarbon optionally containing from 1-3 heteroatoms selected from oxygen, sulfur, and nitrogen, and "n" and "m" are each independently integers selected to satisfy the foregoing ratios of maleic anhydride monomer to styrene monomer, to provide a molecular weight between about 2,500 and about 80,000 Daltons. IN one embodiment, X is —O—. In one embodiment X is —NH—. In one embodiment X is —NR*—. In one embodiment, R* is a group of the form —$(CH_2)_{1-6}$—NH—$(CH_2)_{0-6}$CH_3 or a group —$(CH_2)_{1-6}$—N$((CH_2)_{1-6}CH_3)_2$.

In one embodiment, the styrene-maleic anhydride copolymer comprises an alternating copolymer. In another embodiment, "n" and "m" are each independently integers selected to provide any of the monomer ratios described herein and to provide a molecular weight between about 5,000 and about 10,000 Daltons.

In yet another embodiment, the styrene-maleic anhydride copolymer in the compositions of the invention comprises the repeat unit of Formula (II):

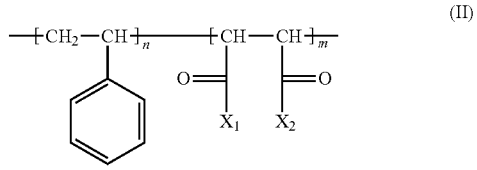

wherein, $X_1$ and $X_2$ are atoms or moieties selected to form carboxyl groups, carboxylate groups, esters, and amides. In one embodiment, $X_1$ and $X_2$ are independently selected from —OH, —OZ, —OR—$NH_2$, and —NHR*, wherein R and R* are independently a $C_{1-12}$ hydrocarbon (e.g., $C_1$-$C_8$, $C_2$-$C_6$, etc.) optionally containing from 1-3 heteroatoms (e.g., one, two, or three heteroatoms) selected from oxygen, sulfur, and nitrogen, and Z is a cation for example from $Na^+$ or $NH_4^+$, where "n" and "m" are each independently integers selected to provide a molecular weight between about 2,500 and about 80,000 Daltons and to provide any of the monomer ratios described herein. In some embodiments, "n" and "m" are each independently integers selected to provide a molecular weight between about 5,000 and about 10,000 Daltons. In some embodiments, one of $X_1$ or $X_2$ is a group —$NH_2$ and the other of $X_1$ or $X_2$ is —OH or —OZ. In one embodiment, $X_1$ and $X_2$ are OZ (where Z is typically sodium or ammonium). In one embodiment, $X_1$ and $X_2$ are OH. IN one embodiment, $X_1$ and $X_2$ are independently groups R. In one embodiment, $X_1$ is R and $X_2$OH. In one embodiment, $X_1$ is —NHR* and $X_2$ is OH. In one embodiment, the styrene maleic anhydride copolymer comprises an alternating copolymer.

Another aspect of the invention provides a pigment grind capable of exhibiting a color change prepared according to the methods described herein.

In still another embodiment of the invention, cosmetic compositions and personal care products are provided that comprise a pigmented composition capable of exhibiting a color change, such as a pigment grind comprising pigment particulates in a carrier and a styrene-maleic anhydride copolymer. The cosmetic compositions may be in the form of any cosmetic or personal care product to impart color to a human integument. For example, the cosmetic composition may be, without limitation, in the form of lipstick, lip color, lip gloss, nail polish, foundation, face powder, body powder, concealer, blush, eye shadow, eye liner, mascara, or bronzer. The personal care product may be in any suitable form to impart color to a human integument. For example, the personal care product may include day creams or lotions, night creams or lotions, sunscreen lotions, creams, or oils and other SPF products, moisturizers, salves, ointments, gels, body milks, artificial tanning compositions, depilatories, etc.

Cosmetic products generally include a color component in the form of pigmented solid particles for giving it its characteristic color or "shade," or other solid particles for giving it a desired texture or sheen (e.g., mica, pearlescents, spherical polymers, optical diffusers, waxes, etc.) with the color component being dispersed throughout a suitable base or vehicle. For example, in the case of lipstick the coloring agent or pigmented ingredients may be dispersed in a base comprising a mixture of waxes (typically from 5-20% by weight), emollients, and moisturizers, whereas, in the case of blush, the pigmented solids may be dispersed in a base comprising a mixture of talc, kaolin, and various known binders.

The cosmetic compositions and personal care products of the invention may also comprise any conventional components, including fillers and cosmetic powders, film forming polymers, gelling agents, waxes, thickeners, conditioners, actives, solvents, emulsifiers, humectants, emollients, pH adjusters, antioxidants, preservatives, fragrances, and the like. In one embodiment, the cosmetic compositions comprise a cosmetic ingredient selected from waxes, gelling agents, emollients, and film forming polymers.

The gelling agent may comprise, for example, one or more of a silicone resin, including Dimethicone/Vinyl Dimethicone crosspolymer, silicone T-resins, ETPEA, polyamides, cellulose ethers (e.g., methyl cellulose or ethyl cellulose) and the like. Thickeners such as acrylates copolymers, hydroxyalkyl cellulose, carboxymethylcellulose, carbomers, and vegetable gums such as xanthan gum may be included.

The compositions may include natural or synthetic film-forming polymers. Suitable polymeric film formers include polyolefins, silicone polymers (e.g., dimethicones, dimethiconols, amodimethicones, silicone resins, etc.), (meth)acrylates, alkyl (meth)acrylates, polyurethanes, fluoropolymers, silicone polyurethanes, and silicone acrylates such as acrylates/dimethicone copolymers. In some embodiments, it may be desirable to add a hydrophilic or water-soluble film former (e.g., cellulosics, polysaccharides, polyquaterniums (such as polyquaternium-37 (INCI), etc.) to the composition to improve spreading, emulsion stability, aesthetic look and feel, etc. Elastomers formed from ethylene, propylene, butylene, and/or styrene monomers may also be useful.

Suitable emollients include, without limitation, isopropyl myristate, petrolatum, volatile or non-volatile silicones oils (e.g., methicone, dimethicone), ester oils, mineral oils, hydrocarbon oils, and fatty acid esters.

Suitable humectants such as polyols (e.g., glycols), including without limitation, glycerin, propylene glycol, ethoxydiglycol, butylene glycol, pentylene glycol, hexylene glycol, caprylyl glycol, and the like. These will typically be added in amount from about 0.001 to about 5% by weight.

In another embodiment, the compositions of the invention may also include one or more of the following: a skin penetration enhancer; a skin plumper, such as palmitoyl oligopeptide, collagen, collagen and/or glycosaminoglycan (GAG) enhancing agents; an exfoliating agent; and an antioxidant (e.g., TDPA).

Suitable waxes that may be used alone or in combination include, without limitation, natural waxes, mineral waxes, and synthetic waxes. Natural waxes are those of animal origin, including, without limitation, beeswax, spermaceti, lanolin, and shellac wax, and those of vegetable origin, including, without limitation, carnauba, candelilla, bayberry, and sugarcane wax, Mineral waxes contemplated to be useful include, without limitation, ozokerite, ceresin, montan, paraffin, microcrystalline, petroleum, and petrolatum waxes.

Suitable synthetic waxes include, for example, polyethylene glycols such as PEG-18, PEG-20, PEG-32, PEG-75, PEG-90, PEG-100, and PEG-180 which are sold under the tradename CARBOWAX® (The Dow Chemical Company). Carbowax 1000 has a molecular weight range of 950 to 1,050 and a melting point of about 38° C., Carbowax 1450 has a molecular weight range of about 1,305 to 1,595 and a melting point of about 56° C., Carbowax 3350 has a molecular weight range of 3,015 to 3,685 and a melting point of about 56. ° C., and Carbowax 8000 has a molecular weight range of 7,000 to 9,000 and a melting point of about 61° C.

Additional suitable synthetic waxes include Fischer Tropsch (FT) waxes and polyolefin waxes, such as ethylene homopolymers, ethylene-propylene copolymers, and ethylene-hexene copolymers. Representative ethylene homopolymer waxes are commercially available under the tradename POLYWAX® Polyethylene (Baker Hughes Incorporated) with melting points ranging from 80° C. to 132° C. Commercially available ethylene-α-olefin copolymer waxes include those sold under the tradename PETROLITE® Copolymers (Baker Hughes Incorporated) with melting points ranging from 95° C. to 115° C.

The compositions of the invention may optionally include additional skin benefit agents such as antioxidants (e.g., BHT, ascorbic acid, sodium ascorbate, ascorbyl palmitate, beta-carotene, etc.), vitamins (e.g., tocopherol, tocopheryl acetate, etc.), alpha-hydroxy acids (e.g., glycolic acid), beta-hydroxy acids (e.g., salicylic acid), retinoids (e.g., retinoic acid, all-trans-retinoic acid, retinaldehyde, retinol, and retinol esters such as acetates or palmitates), other anti-aging ingredients (e.g., collagen stimulators, collagenase inhibitors, elastase inhibitors), depigmenting agents (e.g., TDPA, hydroquinone, kojic acid), barrier function enhancing agents (e.g., ceramides, glycerides, cholesterol and its esters, alpha-hydroxy and omega-hydroxy fatty acids and esters thereof, etc.), exfoliating agents, estrogen synthetase stimulating compounds (e.g., caffeine and derivatives), compounds capable of inhibiting 5 alpha-reductase activity (e.g., linolenic acid, linoleic acid, finasteride, and mixtures thereof). These benefit agents will typically be present, if at all, in amounts between about 0.001% and about 10% by weight of the composition.

A sunscreen (organic and/or inorganic) may be included to protect the skin from damaging ultraviolet rays. In an illustrative embodiment of the present disclosure, the sunscreen provides both UVA and UVB protection, by using either a single sunscreen or a combination of sunscreens. Among the sunscreens that can be employed in the present compositions are avobenzone, cinnamic acid derivatives (such as octyl-methoxy cinnamate), octyl salicylate, oxybenzone, octocrylene, titanium dioxide, zinc oxide, or any mixtures thereof. The sunscreen may be present from about 1% by weight to about 30% by weight of the total weight of the composition.

Suitable fillers may include talc, silica, alumina, zinc stearate, mica, kaolin, nylon (in particular orgasol) powder, polyethylene powder, polypropylene powder, acrylates powders, Teflon, starch, boron nitride, copolymer microspheres such as Expancel (Nobel Industrie), Polytrap (Dow Corning), and silicone resin microbeads (Tospearl from Toshiba).

Other fillers that may be used in the compositions of the invention include inorganic powders such as chalk, fumed silica, fumed alumina, calcium oxide, calcium carbonate, magnesium oxide, magnesium carbonate, Fuller's earth, attapulgite, bentonite, muscovite, phlogopite, synthetic mica, lepidolite, hectorite, biotite, lithia mica, vermiculite, aluminum silicate, aluminum magnesium silicate, diatomaceous earth, starch, alkyl and/or trialkyl aryl ammonium smectites, chemically modified magnesium aluminum silicate, organically modified montmorillonite clay, hydrated aluminum silicate, hydrated silica, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicon dioxide; organic powder, cyclodextrin, methyl polymethacrylate powder, copolymer powder of styrene and acrylic acid, benzoguanamine resin powder, and poly(ethylene tetrafluoride) powder.

The compositions may further include an emulsifier. The amount of emulsifier will typically be from about 0.001 to about 10% by weight, but preferably will range from about 0.01 to about 5% by weight, and most preferably about 0.1 to about 1% by weight, based upon the total weight of the composition. The emulsifier may be ionic, zwitterionic, or nonionic. Suitable emulsifiers include those of the polyethoxylated type (e.g., polyoxyethylene ethers or esters), polydiorganosiloxane-polyoxyalkylene block copolymers (e.g., dimethicone copolyol), Steareth-20, Steareth-21, fatty alcohols (e.g., Cetearyl Alcohol), Polyoxethylene sorbitan fatty acid esters (i.e., polysorbates), and Hydrogenated Castor Oil, to name a few. Additional emulsifiers are provided in the INCI Ingredient Dictionary and Handbook 11th Edition 2006, the disclosure of which is hereby incorporated by reference.

The compositions may comprise a cationic polymer. Cationic polymers include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, and guar hydroxypropyltrimonium chloride. When present, the cationic polymer will typically comprise an amount of about 0.1% to about 15% by weight of the composition. In other embodiments the compositions may contain an amount of cationic (quaternium) ingredients that are anhydrous or have very low level of water, e.g., less than 1% by weight. Other suitable quaternium compounds include, without limitation, Polyquaternium-(INCI), Silicone Quaternium-18 (INCI), PEG-2 Dimeadowfoamamidoethylmonium Methosulfate and Hexylene Glycol (INCI), and Cetrimonium Chloride (INCI), to name a few. Such quaternium compounds, if present, will typically comprise from about 0.05% to about 5% by weight of the total composition, and more typically, from about 0.1% to about 1.5% by weight.

The compositions may also comprise monomer quaternary ammonium compounds such as, for example, alkyltrimethy-lammonium chlorides, dialkylmethyl-ammonium chlorides, alkyldimethylbenzylammonium chlorides, and alkylpyridinium chlorides. In one embodiment, the composition comprises at least one conditioning agent selected from the group consisting of polyquaterniums, cationic polymers, cationic surfactants, non-volatile dimethicone oils, dimethiconols, amodimethicones, ester oils, fatty alcohols, cationic gums and cellulosics, amidoamines, cetrimonium chloride, behentrimonium chloride, stearamidopropyl dimethylamine, polyesteramines, and cationically charge-modified polymers derived from guar gum, cellulose, proteins, polypeptides, chitosan, lanolin, starches and amino silicones.

The compositions may include a nonionic surfactant such as Laureth-23, Ceteth-10, Ceteth-20, IsoCeteth-20, Steareth-20, Oleth-10, Oleth-20, or alkyl polyglucose. The nonionic surfactant may be formed from a fatty alcohol, a fatty acid, or a glyceride with a C8 to C24 carbon chain. The compositions of the invention can further comprise proteins, peptides, and amino acids including hydrolyzed soy protein, lauryldimonium hydrolyzed soy protein (cationic Soya protein), wheat amino acids, corn, wheat, milk, or silk proteins, collagens, keratins, taurine and arginine hydrochloride, etc.

The cosmetic compositions of the invention may optionally include one or more agents that provide or enhance shine on a keratin fiber. Shine enhancing agents will typically have a refractive index greater than about 1.4, preferably greater than about 1.5 when measured as a film at 25° C. Suitable shine enhancing agents include without limitation, polyols, fatty esters, silicone phenylpropyldimethylsiloxysilicate, polybutene, polyisobutene, hydrogenated polyisobutene, hydrogenated polycyclopentadiene, propyl phenyl silsesquioxane resins; lauryl methicone copolyol, perfluorononyl dimethicone, dimethicone/trisiloxane, methyl trimethicone, and combinations thereof. In one embodiment, the composition will comprise a shine-enhancing agent in an amount from about 0.1% to about 10% by weight, based on the total weight of the composition.

The compositions may also comprise a preservative or anti-microbial agent, for example, methylchloroisothiazolinone, methylisothiazolinone, methylparaben, propylparaben, phenoxyethanol, or caprylyl glycol.

The compositions of the invention will typically include a cosmetically or dermatologically acceptable vehicle that is substantially anhydrous. As used herein, "substantially anhydrous" means comprising less than 5% water. In other embodiments, the vehicle and/or the entire cosmetic or personal care composition comprises less than 4%, less than 3%, less than 2%, less than 1%, less than 0.5%, or less than 0.1% by weight water.

The vehicle may be in the form of, for example, a serum, a cream, a lotion, a gel, or a stick, and may comprise an emulsion (e.g., polyol-in-silicone, silicone-in-polyol emulsion, etc.), or may comprise an ethanolic vehicle, silicone (e.g., cyclomethicone, dimethicone, etc.), hydrocarbon (e.g., petrolatum, isododecane, etc.), ester oil (e.g., isopropyl myristate, myristyl myristate), or the like. The vehicle may further comprise an emulsifier, gelling agent, structuring agent, rheology modifier (e.g., a thickener), film former, or the like. The vehicle may comprise from about 25% to about 99% by weight of the composition.

The compositions may, for example, comprise (1) from about 1% to about 75% (e.g., about 1-10%, about 10-20%, about 30-40%, about 40-50%, or about 50-60%) by weight of an oil, including without limitation hydrocarbons (e.g., isododecane, squalane, etc.), fatty alcohols, ester oils, and silicone oils; (2) from about 0.5% to about 20% (e.g., about 0.5-2.5%, or about 2.5%-5%, or about 5-10%, or about 10-15%, or about 15-20%) by weight of a film-forming polymer, including a polyurethane film former, such as bis-PEG-1 dimethicone-propylene glycol/IPDI copolymer; (3) from about 0.1% to about 25% (e.g., about 0.5%-5%, or about 5-10%, or about 10-15%, or about 15-20%) by weight of a gelling agent; (4) from about 0.1% to about 15% (e.g., about 0.1-1%, or about 1-2.5%, or about 2.5-5%, or about 5-10%, or about 10-15%) by weight of a wax (e.g., ozokerite, microcrystalline wax, polyethylene wax, etc.); (5) from about 1% to about 35% (e.g., about 8% to about 20%) by weight pigments (inclusive of all pigments in any pigment grind); and/or (6) from about 0.1% to about 2.5% (e.g., about 0.1-0.5%, about 0.5-1%, or about 1-2.5%) by weight caprylyl glycol.

In another aspect of the invention, a method is provided of achieving a color change in a pigmented composition such as a cosmetic or a personal care product applied to a human integument. The method comprises applying to the integument a film of a cosmetic composition or personal care product described herein. The method further comprises applying water or an aqueous solution to the film and applying shear and/or pressure (e.g., by rubbing it) until a pigmented change in one or more optical properties (e.g., color, hue, renewed color, etc.) is achieved. The amount of water added is in an amount sufficient to achieve a visible color change. For example, in some embodiments, water is applied to a cosmetic film in an amount from about 0.01 mg/cm$^2$ to about 100 mg/cm$^2$ or more. The amount of pressure applied during rubbing and the duration of rubbing needed to achieve a change in one or more optical properties will vary based on the particular pigmented composition, and may vary based on the amount of change in optical attributes that is desired. In some embodiments, a longer duration of rubbing will cause a greater color change, and in some embodiments, applying more pressure will yield a greater color change.

The application of pressure and/or shear (e.g., by rubbing) and water to the films of compositions and personal care products of the invention can cause color renewal, a change in color, a change in hue, a change in shade, or a change in intensity of the color.

The cosmetic compositions and personal care products of the invention are applied to the human integumentary system, including, skin, lips, nails, hair, and other keratinous surfaces. As used herein, the term "keratinous surface" refers to keratin-containing portions of the human integumentary system, which includes, but is not limited to, skin, lips, hair (including hair of the scalp, eyelashes, eyebrows, facial hair, and body hair such as hair of the arms, legs, etc.), and nails (toenails, fingernails, cuticles, etc.) of mammalians, preferably humans.

In some embodiments, cosmetics or personal care products capable of exhibiting a color change can be applied to any area of the skin, and preferably on the face, the neck, the hands, the feet, or other areas of the body, such as arms, legs, and back.

In one embodiment, a lipstick capable of exhibiting a color change comprising a pigmented composition of the invention (e.g., a pigment grind) is applied to the lips to impart a particular color. At a later time, a clear, aqueous topcoat is applied to the lips and rubbed, thereby effecting a change in color, color intensity, or hue. In one embodiment, the application of the topcoat renews or partially or substantially restores the color of the lipstick to its original color. In another embodiment, application of the clear, aqueous topcoat causes a sheer lipstick to become less sheer or even opaque.

In one embodiment, a mascara capable of exhibiting a color change comprising a pigmented composition of the invention (e.g., a pigment grind) is applied to the eye lashes as a film thereon to impart a particular color. At a later time, a clear, aqueous topcoat is applied to the eye lashes and rubbed, thereby effecting a change in color, color intensity, or hue. In one embodiment, the application of the topcoat renews or partially or substantially restores the color of the mascara to its original color. In another embodiment, application of the clear, aqueous topcoat causes a sheer mascara to become less sheer or even opaque.

In one embodiment, an eye shadow capable of exhibiting a color change comprising a pigmented composition of the invention (e.g., a pigment grind) is applied to the eyelids to impart a particular color. At a later time, a clear, aqueous topcoat is applied to the eyelids and rubbed, thereby effecting a change in color, color intensity, or hue. In one embodiment, the application of the topcoat renews or partially or substantially restores the color of the eye shadow to its original color. In another embodiment, application of the clear, aqueous topcoat causes a sheer eye shadow to become less sheer or even opaque.

In another embodiment, a blush capable of exhibiting a color change comprising a pigmented composition of the invention (e.g., a pigment grind) is applied to the skin of the face to impart a particular color. At a later time, a clear, aqueous topcoat is applied to the face and rubbed, thereby effecting a change in color, color intensity, or hue. In one embodiment, the application of the topcoat renews or partially or substantially restores the color of the blush to its original color. In another embodiment, application of the clear, aqueous topcoat causes a sheer blush to become less sheer or even opaque.

In yet other embodiments, the aqueous topcoat that is later applied and rubbed is not clear (i.e., it has color provided by one or more pigments, lakes, or dyes), and causes a change in color, color intensity, or hue of the lipstick, mascara, eye shadow, blush, etc.

In another embodiment, a composition (e.g., a skin cream) capable of exhibiting a color change comprising a pigmented composition of the invention (e.g., a pigment grind) is applied to an integument (e.g., the skin) to impart a film thereon. The composition may be provided as a dual-chamber product such that the portion containing a pigment grind of the invention is held in one chamber in an anhydrous or substantially anhydrous formulation, and an aqueous portion is held in the other chamber. When the product is dispensed (e.g., through a pump), the compositions from each chamber are mixed together, and upon rubbing the product, e.g., into the skin, a color change is achieved (e.g., a bronze color on the skin).

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, §201(i).

EXAMPLES

Example 1

Two lip color products were prepared according to the formulas in Table 1—a Control Lipstick and a Test Lipstick. For each of the lipsticks, a lipstick base was prepared and a pigment grind was prepared, using the ingredients listed in Table 1. The inventive pigment grind, including castor oil, red iron oxide and styrene maleic anhydride (SMA) copolymer was first prepared by subjecting the ingredients to shear in a 3-roll mixer at 500 min$^{-1}$ for 30 minutes at 25° C. The inventive pigment grind was used in the Test Lipstick. The pigment grind was added to the lipstick base, and then mixed at 500 min$^{-1}$ for 3 hours at 95° C. The mixture was then cooled for 15 minutes at 6° C. and was then allowed to sit overnight. The Control Lipstick was prepared identically except that no SMA copolymer was added (in the Test Lipstick, SMA copolymer was added in the amount of 2% by weight of total composition). Draw downs (1 mil thick) were made of the Control and Test Lipsticks. The films were then evaluated using a Nikon 50i polarizing light microscope with a 10× objective.

The Control Lipstick film showed a general lack of agglomerate (i.e., it was a substantially homogenous dispersion of pigments). The Test Lipstick film, on the other hand, showed the presence of large agglomerates of pigment. This suggests that the SMA copolymer forms larger agglomerates of pigments in the pigment grind. Thus, without wishing to be bound by theory, it is believed that the color change phenomenon may arise because a significant surface area of pigment is obscured within the agglomerates and becomes released or at least partially exposed when the agglomerates are broken down by water and/or shear.

The ability of the Test film to change color was confirmed by wetting the surface with water and rubbing with a finger. The film visibly darkened and became more opaque in the area of rubbing. In contrast, no color change was observed in the Control Lipstick.

TABLE 1

|  | Control Lipstick (%) | Test Lipstick (SMA added) (%) |
|---|---|---|
| LIPSTICK BASE | | |
| Diglyceryl Diisostearate | 10.51 | 10.51 |
| Glyceryl Triacetyl Hydroxystearate | 7.91 | 7.91 |
| Squalane | 10.01 | 10.01 |
| Myristyl Lactate | 7.51 | 7.51 |
| C10-30 Cholesterol/Lanosterol Esters | 4.50 | 4.50 |
| Polybutene | 3.20 | 3.20 |
| Polyglycerol Diisostearate | 3.00 | 3.00 |
| Tocopheryl Acetate-Syn | 0.05 | 0.05 |
| PPG-51/SMDI Copolymer | 2.50 | 2.50 |
| Silica-High Oil Absorbing | 0.50 | 0.50 |
| Stearyl Dimethicone | 2.50 | 2.50 |
| Caprylyl Glycol | 0.50 | 0.50 |
| C12-15 Alcohols Benzoate | 0.15 | 0.15 |
| Lithium Magnesium Silicate | 0.10 | 0.10 |
| Ozokerite Wax | 5.51 | 5.51 |
| Micro Wax White | 5.01 | 5.01 |
| Polyethylene-Linear Wax | 3.00 | 3.00 |
| Ethylhexyl-Methoxycinnamate | 1.00 | 1.00 |
| Jojoba Oil Low Odor | 0.10 | 0.10 |
| PIGMENT GRIND | | |
| Castor Oil | 17.50 | 15.50 |
| Red Iron Oxide | 15.00 | 15.00 |
| SMA Polymer | 0.00 | 2.00 |
| TOTAL | 100 | 100 |

Example 2

Several lip color products were prepared according to the formulations described in Example 1. The lipstick identified as "control" contained no SMA polymers in the pigment grind, whereas all other lipsticks contained SMA copolymers (in the amount of 2% by weight of total composition).

Styrene maleic anhydride copolymers were obtained from Polyscope, and those used in this Example contained varying ratios of styrene to maleic anhydride, and were prepared as different salt forms. XIRAN® SL40005 contains 42% maleic anhydride and 58% styrene, with a molecular weight of 5 kD and a $T_g$ of 130° C. The N30 form of XIRAN® SL40005 is an ammonium salt solution that is slightly alkaline. The N30 Amic acid form of XIRAN® SL40005 (i.e., $X_1$ is $NH_2$ and $X_2$ is OH in Formula (II)) is slightly acidic. The S40 form of XIRAN® SL40005 is a sodium salt derivative of the anhydride in alkaline solution. XIRAN® SL25010 contains 25% maleic anhydride and 75% styrene, with a molecular weight of 10 kD and a $T_g$ of 130° C. The N15 form of XIRAN® SL25010 is an ammonium salt derivative of the anhydride that is slightly alkaline. The S25 form of XIRAN® SL25010 is a sodium salt derivative that is in alkaline solution.

The difference in color between control lipstick and lipsticks with SMA polymers added to the pigment grind was measured to determine ΔE. 1 mil draw-downs were completed on white Leneta cards and were allowed to dry for 4 hours. 10 L*, a*, b* readings were taken for each sample using a Konita Minolta spectrophotometer, the average was calculated, and ΔE values for each sample were determined. ΔE values equal to or above 15 were shown to have a perceivable color change during this procedure. Perceivable color change was determined by adding water and shear (rubbing in a circular motion with a finger) to the lipstick draw downs. Results from these experiments are shown in Table 2.

TABLE 2

| Styrene maleic anhydride | Dose (%) | ΔE | Color Change |
|---|---|---|---|
| Control | 0.00 | 0.00 ± 0.45 | No |
| XIRAN SL40005 N30 Amic Acid | 2.00 | 51.12 ± 1.48 | Yes |
| XIRAN SL40005 N30 | 2.00 | 43.54 ± 0.91 | Yes |
| XIRAN SL40005 S40 | 2.00 | 48.10 ± 1.36 | Yes |
| XIRAN SL25010 N15 | 2.00 | 47.26 ± 1.23 | Yes |
| XIRAN SL25010 S25 | 2.00 | 46.72 ± 1.28 | Yes |

All of the lip color products prepared with 2% (by weight of the total composition) SMA polymers yielded perceptible color change with the application of water and shear. The greatest ΔE was observed when the pigment grind contained 2% XIRAN SL40005 N30 Amic Acid.

Example 3

Lip color products were prepared according to Example 1, using varying amounts of XIRAN® SL40005 N30 Amic Acid as the SMA polymer added to the pigment grind. Where the % of SMA polymer deviates from 2% by weight of the total cosmetic composition, the difference is made up for in the amount of castor oil added to the pigment grind. Color change and ΔE values were determined according to the same methods described in Example 2. The results of these experiments are shown in Table 3 below.

TABLE 3

| | Dose (%) | ΔE | Color Change |
|---|---|---|---|
| XIRAN SL40005 N30 Amic Acid | 0.00 | 0.00 ± 0.44 | No |
| | 0.10 | 1.65 ± 0.43 | No |
| | 0.75 | 24.84 ± 0.58 | Yes |
| | 1.50 | 44.16 ± 0.98 | Yes |
| | 2.00 | 48.72 ± 1.20 | Yes |
| | 5.00 | 50.03 ± 0.63 | Yes |
| | 10.00 | 22.74 ± 0.34 | Yes |
| | 15.00 | 14.01 ± 0.37 | No |

The data in Table 3 demonstrate a dose effect of the XIRAN® SL40005 N30 Amic Acid form of SMA polymer, with the highest ΔE values obtained at 5% of the total lip color cosmetic. Once the SMA polymer reached 15%, ΔE dropped below 15, and a color change was no longer observed in this particular formulation.

Example 4

Several lip color products were prepared according to Example 1, using varying amounts of XIRAN® SL40005 N30 Amic Acid as the SMA polymer added to the pigment grind, and using different pigments in the pigment grind. Where the % of SMA polymer deviates from 2% by weight of the total cosmetic composition, the difference is made up for in the amount of castor oil added to the pigment grind. Color change and ΔE values were determined according to the same methods described in Example 2. The results of these experiments are shown in Table 4 below.

TABLE 4

| | Dose (%) | ΔE | Color Change |
|---|---|---|---|
| Control | 0.00 | 0.00 ± 0.56 | No |
| Titanium Dioxide | 2.00 | 26.62 ± 4.82 | Yes |
| Yellow Iron Oxide | 15.00 | 12.59 ± 1.38 | No |
| Red Iron Oxide | 2.00 | 51.12 ± 1.48 | Yes |
| Red 7 Ca Lake | 15.00 | 38.79 ± 4.21 | Yes |
| Violet Mango | 2.00 | 25.30 ± 2.20 | Yes |
| Black Iron Oxide | 2.00 | 41.47 ± 9.83 | Yes |

The data from these experiments demonstrate that varying amount of XIRAN® SL40005 N30 Amic Acid used in pigment grinds with different types of pigments can be effective in varying ΔE and in causing an observed color change.

Example 5

Several lip color products were prepared according to Example 1, using 2% by weight of the total composition XIRAN® SL40005 N30 Amic Acid as the SMA polymer added to the pigment grind. Also added to the lip color products was an additional (conventional) pigment grind with the same pigment (red iron oxide) and castor oil, but without the addition of an SMA polymer. The ratio of pigment grind without SMA polymer to pigment grind with 2% SMA polymer was varied, and is identified in Table 5 below. Color change and ΔE values were determined according to the same methods described in Example 2.

TABLE 5

| (Grind with 0 SMA): (Grind + 2% SMA) | Dose (%) | ΔE | Color Change |
|---|---|---|---|
| 1:0 | 0.00 | 0.00 ± 0.50 | No |
| 0:1 | 1.00 | 32.58 ± 0.85 | Yes |
| 5:5 | 1.00 | 10.80 ± 0.38 | No |
| 4:6 | 1.20 | 12.23 ± 0.49 | No |
| 3:7 | 1.40 | 18.74 ± 0.58 | No |
| 2:8 | 1.60 | 30.56 ± 0.63 | Yes |
| 1:9 | 1.80 | 40.38 ± 0.81 | Yes |
| 0:1 | 2.00 | 50.32 ± 1.92 | Yes |

The data from these experiments demonstrate that a cosmetic product containing a pigment grind with SMA polymers and a pigment grind without SMA polymers must provide the two pigment grinds in an optimal ratio so that color change is still perceivable. That is, there must be enough inventive pigment grind (with SMA polymer) so that a color change is still perceptible against the background of the conventional pigment grind (i.e., that contains no SMA polymer). The two pigment grinds used in any cosmetic or personal care product (i.e., the inventive pigment grind with SMA polymer and the conventional pigment grind without SMA polymer) can comprise the same pigments or can comprise different pigments.

Example 6

A lip color product was prepared according to Example 1, using 2% by weight of the total composition XIRAN® SL40005 N30 Amic Acid as the SMA polymer, except that in this case, the SMA polymer was not added to the pigment grind, but rather was added after the lipstick base and pigment grind were already mixed together. The results, shown in Table 6 below, show that ΔE is low (below 15), and that the color change effect imparted by the SMA polymer (when added to a pigment grind) is not observed when the SMA polymer is added after the pigment grind has already been made and added to the cosmetic formulation.

TABLE 6

| | Dose (%) | ΔE | Color Change |
|---|---|---|---|
| XIRAN SL40005 N30 Amic Acid | 2.00 | 1.68 ± 0.39 | No |

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described therein will become apparent to those skilled in the art from the foregoing description. Such modifications are also intended to fall within the scope of the appended claims. All publications cited herein are incorporated by reference in their entirety.

What is claimed is:

1. A method of achieving a color change in a cosmetic composition applied to a human integument comprising:
   (1) applying to said human integument a substantially anhydrous cosmetic composition to form a film thereon, wherein said composition comprises:
       (a) one or more cosmetic ingredient selected from waxes, gelling agents, emollients, and film forming polymers; and
       (b) a pigment grind capable of exhibiting a color change, prepared by dispersing, under shear, pigment particulates in a substantially anhydrous carrier in the presence of a styrene maleic anhydride copolymer; and
   (2) applying water to said film and rubbing it until a visible color change is achieved.

2. A method according to claim 1, wherein the styrene maleic anhydride copolymer comprises the following repeat unit:

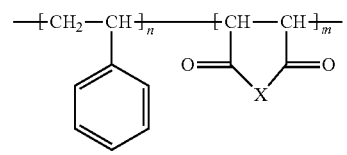

wherein, X is selected from —O—, —NH—, or —NR*—, where R* is a $C_{1-12}$ hydrocarbon optionally containing from 1-3 heteroatoms selected from oxygen, sulfur, and nitrogen, and "n" and "m" are each independently integers selected to provide a molecular weight between about 2,500 and about 80,000 Daltons.

3. The method according to claim 1, wherein said pigment grind comprises: from about 20% to about 80% by weight carrier, from about 20% to about 80% by weight pigment, and from about 0.5% to about 20% by weight styrene-maleic anhydride copolymer.

4. The method according to claim 1, wherein said pigment comprises one or more of titanium dioxide, iron oxide, FD & C lakes, D & C lakes, and carbon black.

5. The method according to claim 1, wherein said pigment comprises iron oxide.

6. The method according to claim 1, wherein said styrene maleic anhydride copolymer is composed of from about 25% to about 50% maleic anhydride monomers and from about 50% to about 75% styrene monomers.

7. The method according to claim 2, wherein said styrene-maleic anhydride copolymer comprises an alternating copolymer.

8. The method according to claim 2, wherein "n" and "m" are each independently integers selected to provide a molecular weight between about 5,000 and about 10,000 Daltons.

9. The method according to claim 1, wherein said styrene-maleic anhydride copolymer comprises the following repeat unit:

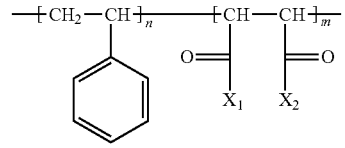

wherein, $X_1$ and $X_2$ are independently selected from —OH, —OZ, —OR—NH$_2$, and —NHR*, wherein R and R* are independently a $C_{1-12}$ hydrocarbon optionally containing from 1-3 heteroatoms selected from oxygen, sulfur, and nitrogen, and Z is a cation selected from $Na^+$ and $NH_4^+$, where "n" and "m" are each independently integers selected to provide a molecular weight between about 2,500 and about 80,000 Daltons.

10. The method according to claim 9 wherein one of $X_1$ or $X_2$ is a group —NH$_2$ and the other of $X_1$ or $X_2$ is —OH.

11. The method according to claim 9, wherein said styrene-maleic anhydride copolymer comprises alternating copolymer.

12. The method according to claim 9, wherein "n" and "m" are each independently integers selected to provide a molecular weight between about 5,000 and about 10,000 Daltons.

13. The method according to claim 1, wherein said shear is applied in a three-roll mill.

* * * * *